United States Patent [19]

Nees

[11] Patent Number: 4,608,342

[45] Date of Patent: Aug. 26, 1986

[54] METHOD OF GROWING A CONFLUENT LAYER OF CELLS ON A POROUS OR SEMI-PERMEABLE SUBSTRATE AND APPARATUS FOR PRACTICING THE METHOD

[76] Inventor: Stephan Nees, Waldwiesenstr. 30b, 8000 München 70, Fed. Rep. of Germany

[21] Appl. No.: 609,841

[22] Filed: May 14, 1984

[30] Foreign Application Priority Data

May 13, 1983 [DE] Fed. Rep. of Germany ....... 3317550

[51] Int. Cl.⁴ .......................... C12N 5/00; C12M 3/00
[52] U.S. Cl. .................................. 435/240; 435/284; 435/285; 435/297
[58] Field of Search ........ 435/283, 284, 287, 297–300, 435/301, 310, 240, 285, 286, 243, 261, 30, 31, 311

[56] References Cited

U.S. PATENT DOCUMENTS

| | | |
|---|---|---|
| 2,677,646 | 5/1954 | Lovell et al. ................. 435/311 |
| 2,879,207 | 3/1959 | Poitras ......................... 435/311 |
| 2,904,857 | 9/1959 | Goetz ............................. 435/30 |
| 2,923,669 | 2/1960 | Poitras ........................... 435/30 |
| 3,275,528 | 9/1966 | Ainis ............................ 435/284 |
| 3,684,660 | 8/1972 | Kereluk et al. .............. 435/297 |
| 3,751,341 | 8/1973 | Seitz et al. ..................... 435/30 |
| 4,024,020 | 5/1977 | Weiss ........................... 435/241 |
| 4,189,470 | 2/1980 | Rose ............................. 424/85 |
| 4,237,218 | 12/1980 | Monthony ....................... 435/2 |
| 4,241,187 | 12/1980 | White ........................... 435/283 |
| 4,242,459 | 12/1980 | Chick ...................... 128/DIG. 3 |
| 4,299,669 | 11/1981 | Obana .......................... 204/1 T |
| 4,308,351 | 12/1981 | Leighton et al. ............. 435/284 |
| 4,335,215 | 6/1982 | Tolbert ........................... 435/41 |
| 4,373,029 | 2/1983 | Nees ............................ 366/214 |
| 4,378,016 | 3/1983 | Loeb ............................. 604/891 |
| 4,384,936 | 5/1983 | Obana ........................... 204/403 |
| 4,391,912 | 7/1983 | Yoshida ........................ 435/241 |
| 4,409,331 | 10/1983 | Lim .............................. 435/178 |
| 4,446,234 | 5/1984 | Russo et al. .................. 435/284 |

FOREIGN PATENT DOCUMENTS 0576167 5/1959 Canada ........................... 435/311

OTHER PUBLICATIONS

Fallon, M. D. et al., J. Immunological Methods, vol. 54, pp. 379–384 (1982).

McCall, E. et al., Thrombosis Research, vol. 24, pp. 417–431 (1981).

Primary Examiner—Lionel M. Shapiro
Assistant Examiner—M. Moskowitz
Attorney, Agent, or Firm—Peter K. Kontler

[57] ABSTRACT

A method and apparatus are disclosed for growing a confluent layer of cells on the surface of a substrate which is held by a holding and positioning device so as to be in the form of a taut, planar substrate having upper and lower exposed surfaces. The device is arranged in a nutrient-containing receptacle which also contains a plate material having a solid upper planar surface extending above the plane of the bottom of the receptacle. The lower layer of the receptacle is in contact with the upper surface of the plate material and cells disposed on the upper surface of the substrate are found to anchor to the substrate and grow to a confluent layer.

13 Claims, 9 Drawing Figures

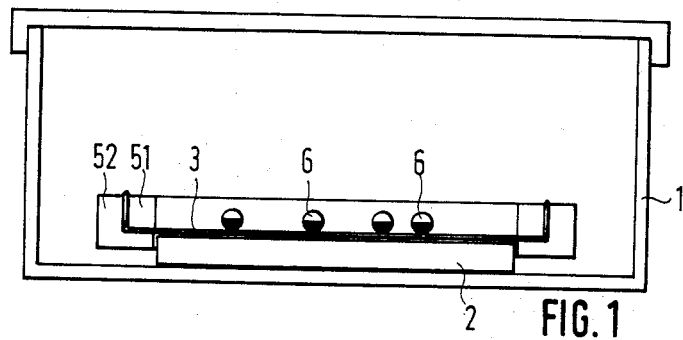
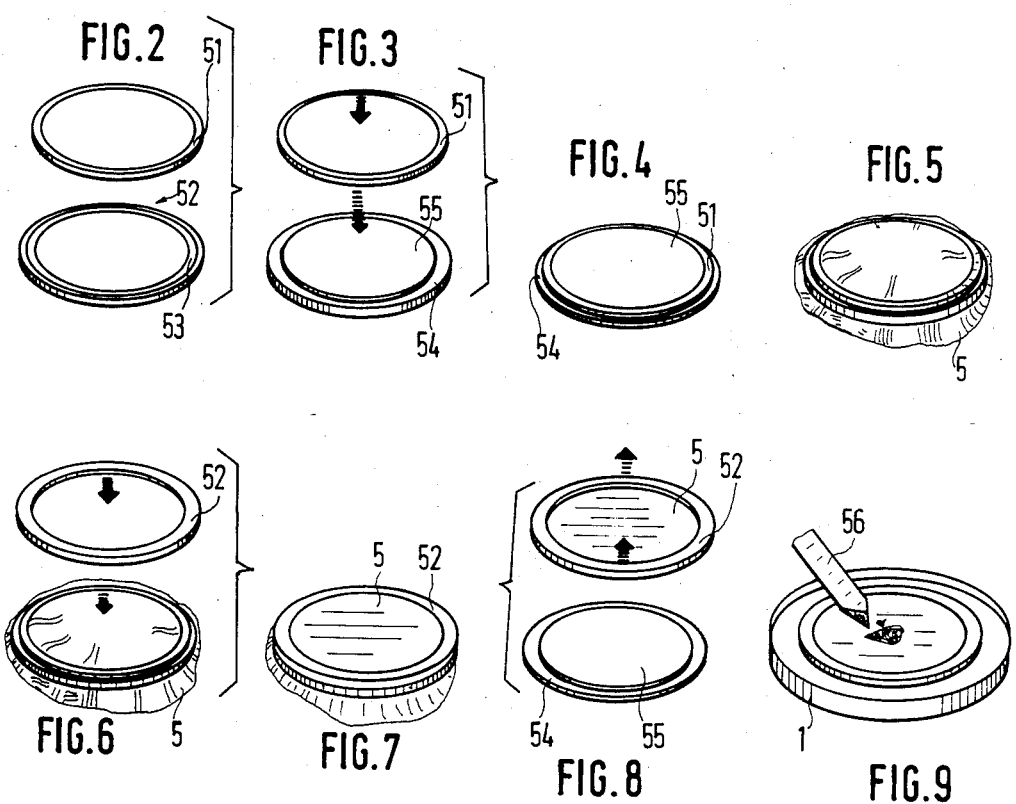

METHOD OF GROWING A CONFLUENT LAYER OF CELLS ON A POROUS OR SEMI-PERMEABLE SUBSTRATE AND APPARATUS FOR PRACTICING THE METHOD

BACKGROUND OF THE INVENTION

The invention relates to a method of growing a confluent layer of cells on a porous or semi-permeable substrate and to apparatus for practicing the method.

For investigating a number of directed processes taking place on confluent cell layers grown on a substrate it is necessary to determine these processes on the apical side of the cell layer as well as those on the basal side thereof. To this end, both sides of a confluent cell layer grown on a porous or semi-permeable substrate must be contacted with perfusion fluid in a double perfusion chamber.

In order to place a substrate having a confluent cell layer grown thereon in a double perfusion chamber, it is necessary to mount the substrate in a holding and tensioning device which then is placed in the double perfusion chamber together with the substrate and the confluent cell layer thereon, the latter having grown for a particular period of time by mitotic division of seed cells.

It has been known to grow confluent cell layers on a porous or semi-permeable substrate by first spreading the substrate on the bottom surface of a so-called Petri dish to cover with one side thereof a medium containing the nutrient required for growing the cells. Thereafter, the seed cells are sown on the substrate and spread to confluence by multiple divisions. However, it has not been possible to this date to grow a confluent cell layer in a Petri dish on one side of a substrate mounted in a holding and tensioning device, said substrate being covered by the medium on both sides. Neither has it been possible to place and tension in a holding and tensioning device a substrate after a confluent cell layer had been grown thereon according to the aforesaid method. In the placing and tensioning process, forces act on the cell layer which cause it to sustain damage so as to disrupt the confluence of the cell layer which is required for the subsequent testing.

It is absolutely necessary to mount the conventional, extremely thin substrates, which may be as thin as 10 to 100 microns, and the confluent cell layers thereon in holding and tensioning means so as to enable the substrate to assume a planar condition in the double perfusion chamber. For this reason, it has not been possible in the past to perform tests in vitro, i.e. outside plant, animal or human bodies in a chamber of this type so as to observe and study directed biological, physiological, biochemical and pharmacological processes on cell layers that form physiological boundaries where corresponding activities take place. The aforesaid processes are enzymatic in nature and involve the discharge of substances to the cell environment in the confluent cell layer, the reception of substances from the cell environment, and the movement of substances from the apical side of the cells through the cell layer to the basal side of the cell, and vice versa. In a double perfusion chamber suited for investigating processes of this kind, both sides of the substrate and of the confluent cell layer thereon must be contacted uniformly and efficiently so that the perfusion fluid flows from both chambers reaching the measurement side may be observed and investigated separately.

SUMMARY OF THE INVENTION

As it has not been possible in the past to grow a confluent cell layer on a substrate in a holding and tensioning device, it is the object of the subject invention to provide a method of growing a confluent cell layer on a substrate mounted on a holding and tensioning device which is placed in a large-size Petri dish until the cell layer has formed and is adapted to be then placed in a double perfusion chamber, and at the same time to provide apparatus for practicing the aforesaid method.

According to the present invention, this and other objects are attained by provision of a method for growing a confluent layer of cells on a substrate surface wherein a taut, planar porous or semi-permeable substrate is arranged in a receptacle containing nutrient medium, with the bottom surface of the planar substrate being in contact with a solid surface of a plate material arranged in the receptacle. A source of cells is placed on the upper substrate surface (i.e., the surface facing away from that surface in contact with the plate material) and a confluent layer of cells is then grown upon that upper surface.

The invention also provides an apparatus for carrying out the foregoing method, as well as a process for constructing the apparatus.

Advantageously, it is now possible for the first time by virtue of the subject invention to grow a confluent cell layer on one side of a porous or semi-permeable substrate mounted on a holding and tensioning device. Thus it has become possible to inventigate in vitro directed biological processes on cell layers.

Also, the inventive method is advantageous in that it is extremely simple and inexpensive in practice.

Another advantage of the subject invention is that the holding and tensioning device used for practicing the inventive method is inexpensive and simple in manufacture.

Another advantage of the invention is that the inventive method permits a confluent cell layer to be grown on a transparent substrate so that the cell layer may be checked microscopically prior to use for the necessary confluence or continuity.

BRIEF DESCRIPTION OF DRAWING

FIG. 1 through 9 represent schematic illustrations of the apparatus and sequence of steps employed in the present invention.

DETAILED DESCRIPTION OF THE INVENTION

The invention will now be explained in detail under reference to the attached drawings.

In early work towards the invention, it was observed that cells cannot properly anchor themselves on one side of a stretched porous or semi-permeable substrate and will die quickly as they do not contact the substrate.

A likely cause of the phenomenon is that the cells synthesize on their basal side substances which must undergo enrichment so as to offer to the cells a possibility of orientation for alignment and subsequent anchoring to the substrate. Where the cells are sown on a porous or smei-permeable substrate kept in the growth medium by its holding and tensioning device, enrichment of the synthesized substances cannot take place as they will migrate into the fluid body below the cells and will be diluted; they may even be decomposed or modified by the action of enzymes.

In the inventive process, the holding and tensioning device mounting the substrate is placed on a plate (made of a material such as glass) in a manner such that the side of the substrate opposite the cells contacts the surface of the glass plate. This way a region will be created between the mutually facing surfaces of the substrate and of the device in which the substances likely to be synthesized by the basal sides of the individual cells and passing through the porous substrate may undergo enrichment. As a result, the upwardly growing cells may orient themselves in a manner that they turn their basal sides towards the porous substrate and finally anchor themselves in place. This way, in the course of a particular growth period, constant cell division of the anchored mother cells will gradually produce a confluent layer of cells.

The process described above is depicted schematically in FIG. 1. The confluent layer of cells is grown in a Petri dish generally shown at 1, which has a cover and contains the nutrient medium required for growing the cells. A ground-glass plate 2, which preferably is disc-shaped, is placed on the bottom of Petri dish 1. Porous substrate 3 is held by an annular holding and tensioning device 51, 52 to be detailed hereinbelow. That holding and tensioning device is constructed so that it will hold the peripheral area of substrate 3 at about the middle of its thickness dimension. The inner diameter of annular holding and tensioning device 51, 52 is selected to be slightly greater than the outer diameter of glass plate 2. As a result, holding and tensioning device 51, 52 may be placed on glass plate 2 so that the side of substrate 3 facing glass plate 2 contacts the surface of the latter. During growth, the upwardly growing cells 6 will assume an orientation such that their basal sides (dark areas) are turned towards the substrate throughout. The substances synthesized by the basal sides of cells 6 may pass through the porous substrate and accumulate in the space between substrate 3 and glass plate 2.

The device for practicing the inventive method will now be explained in greater detail. As shown in FIG. 2, that device preferably comprises two ring members 51, 52. Ring member 52 has along its inner edge a recess 53 extending inwardly from the surface of ring member 52 preferably to about one half its thickness dimension and extending from the inner edge of ring member 52 preferrably to about one half the radial extent thereof. Recess 53 has dimensions such that it may receive ring member 51 with a slight clearance. Ring members 51, 52 preferrably are made of a material resistant to autoclave treatment. For example, the ring members may be of Teflon or Delerin.

As shown in FIG. 3, ring member 51 is placed on a base surface 54 of a nature such that its raised portion 55 fills the space inside ring member 51. This condition is shown in FIG. 4.

As shown in FIG. 5, the substrate material is now placed on the surface of the raised portion 55 and of ring member 51. The substrate preferably comprises a porous filter material consisting of cellulose acetate or polycarbonate and having a porosity of up to 0.5 microns. It is possible also to use as substrate a dialysis membrane.

Thereafter, ring member 52 is pressed onto the assembly shown in FIG. 5 in the direction of the arrows shown in FIG. 6 so that substrate 3 is held fast between ring members 51, 52 in recess 53 and is tensioned to a planar condition in the space enclosed by the ring members above the raised portion 55 of base plate 54. This condition is shown in FIG. 7.

The assembly comprising ring members 51, 52 and substrate 3 may now be removed from base plate 54 (FIG. 8). The portions of the substrate material which project beyond ring members 51, 52 may be removed; preferably they are cut off.

After sterilization, the assembly is placed in Petri dish 1 (cf. the description hereinabove) in a manner such that substrate 3 rests on and contacts glass plate 2.

In another step, cells may be sown directly on the substrate using a pipette, for example, as shown in FIG. 9. Under conventional growth conditions, and depending on the amount and the type of the seed cells, a continuous confluent layer of cells will form on substrate 3 within a period such as two days to eight weeks.

The confluent cell layer so obtained may now be investigated by directly placing the holding and tensioning device in a double perfusion chamber.

As a result, it has been shown that the subject invention makes possible for the first time the provision of confluent cell layers on substrates mounted in holding and tensioning devices. The holding and tensioning devices may be handled and manipulated without risking damage to the cell layers grown thereon.

I claim:

1. A method for growing a confluent layer of cells on a substrate surface, comprising the steps of: providing a porous or semi-permeable substrate in the form of a tensioned, taut, planar substrate having exposed upper and lower surfaces and independently held in such configuration by a tensioning and holding device; providing a receptacle containing fluid nutrient medium for cell growth, said receptacle having a bottom surface and upstanding side walls about the periphery thereof; arranging within said receptacle a body of solid, plate material having a bottom surface in contact with the bottom surface of said receptacle and an upper solid, planar surface extending above the plane of the bottom surface of said receptacle; arranging said holding and tensioning device within said receptacle such that the lower surface of said substrate is in contact with the upper non-porous surface of said plate material and such that the substrate is surrounded by the fluid nutrient medium for cell growth; providing on the upper surface of said substrate a source of cells; and maintaining said arrangement under conditions, and for a time, effective to produce a confluent layer of cells on the upper surface of said substrate, whereby a region is created created between the mutually contacting surfaces of said substrate and said plate material and in said region substances synthesized by the cells in aid of their anchoring to said substrate and passing through the porous or semi-permeable substrate are enriched proximate to the cells and not substantially decomposed, modified or diluted by the surrounding nutrient medium.

2. The method according to claim 1 wherein said plate material consists of a transparent glass body.

3. The method according to claims 1 or 2 wherein said substrate is a porous filter composed of a material selected from the group consisting of cellulose acetate and polycarbonate.

4. The method according to claims 1 or 2 wherein said substrate has a porosity of less than or equal to 0.5 microns.

5. The method according to claims 1 or 2 wherein said substrate comprises a dialysis membrane.

6. A method for growing a confluent layer of cells on a substrate, comprising: providing a porous or semipermeable substrate in the form of a tensioned, taut, planar substrate held about its periphery by a holding and tensioning device, said held substrate having exposed upper and lower surfaces; placing said substrate on a body of solid, plate material such that the lower surface of said substrate is in contact with an upper solid planar surface of said body of plate material; depositing a source of cells on the upper layer of said substrate; providing a source of fluid nutrient medium for cellular growth surrounding said substrate; and maintaining said arrangement under conditions, and for a time, effective to produce a confluent layers of cells on the upper surface of said substrate, whereby a region is created between the mutually contacting surfaces of said substrate and said plate material, and in said region substances synthesized by the cells in aid of their anchoring to said substrate and passing through the porous or semipermeable substrate are enriched proximate to the cells and not substantially decomposed, modified or diluted by the surrounding nutrient medium.

7. An apparatus for growing a confluent layer of cells on a substrate surface, comprising: a receptacle adapted to receive a fluid nutrient medium, having a bottom surface and upstanding side walls about the periphery thereof; a body of solid, plate material arranged within said receptacle and having a bottom surface in contact with the bottom surface of said receptacle and an upper solid planar surface extending above the plane of the bottom surface of said receptacle; and a taut, planar porous or semi-permeable substrate having exposed upper and lower surfaces and held in said taut, planar position by a tensioning and holding device, said tensioning and holding device being arranged within said receptacle such that the lower surface of said substrate is in contact with the upper solid planar surface of said plate material and such that said substrate is adapted to be surrounded by fluid nutrient medium in said receptacle, whereby a region is created between the mutually contacting surfaces of said plate material and said substrate in which substances synthesized by cells in aid of their anchoring to said substrate and passing through said substrate are enriched proximate to the cells and not substantially decomposed, modified or diluted by surrounding nutrient medium, the upper surface of said substrate being adapted to receive a source of cells thereon.

8. The apparatus according to claim 7 wherein said substrate and holding and tensioning device comprises first and second ring members, said second ring member having along its inner edge a recess adapted to receive said first ring member and the peripheral area of said substrate disposed between said first and second ring members.

9. The apparatus according to claim 8 wherein said ring members are circular in shape.

10. The apparatus according to claims 7, 8 or 9 wherein said recess in said second ring member is dimensioned such that the recess covers about one-fourth of the cross-sectional area of said second ring member.

11. The apparatus according to claims 7, 8 or 9 wherein said ring members are circular in shape, said plate material is circular in shape, and wherein the inner diameter of said ring members is slightly greater than the outer diameter of said plate material.

12. The apparatus according to claims 7, 8 or 9 wherein said plate material is composed of glass.

13. A method for constructing an apparatus for growing a confluent layer of cells on a substrate comprising the steps of: providing a first ring member; placing said first ring member on a base plate in a manner such that a raised portion of said base plate fills the space enclosed by said first ring member and the surface of said raised portion facing away from the base plate lies in the same plane as that of the upper surface of said first ring; arranging across the upper surface of said combined first ring and base plate a planar porous or semi-permeable substrate having upper and lower surfaces; providing a second ring member having a recess along its inner edge; urging said second ring member onto the upper surface of said first ring member to clamp said first ring member and edge portions of said substrate in said recess; removing said clamped first and second rings and the substrate therebetween from said base plate; providing a receptacle containing fluid nutrient medium for cells and arranging within said receptacle a plate material having an upper solid planar surface extending above the plane of the bottom surface of said receptacle; and disposing said clamped first and second rings and the substrate therebetween onto the upper surface of said plate material such that the bottom planar surface of said substrate is in contact with said upper surface of said plate material, and such that said substrate is surrounded by said nutrient medium, whereby a region is created between the mutually contacting surfaces of said plate material and said substrate in which substances synthesized by cells in aid of their anchoring to said substrate and passing through said substrate are enriched proximate to the cells and not substantially decomposed, modified or diluted by surrounding nutrient medium.

* * * * *